United States Patent [19]

Shimizu et al.

[11] Patent Number: 4,914,242

[45] Date of Patent: Apr. 3, 1990

[54] PROCESS FOR PREPARING 3-ETHYLBENZOPHENONE

[75] Inventors: Isoo Shimizu; Yasuo Matsumura, both of Yokohama; Yutaka Arai, Tokyo, all of Japan

[73] Assignee: Nippon Petrochemicals Company, Limited, Tokyo, Japan

[21] Appl. No.: 294,694

[22] PCT Filed: Mar. 24, 1988

[86] PCT No.: PCT/JP88/00303

§ 371 Date: Nov. 23, 1988

§ 102(e) Date: Nov. 23, 1988

[87] PCT Pub. No.: WO88/07517

PCT Pub. Date: Oct. 6, 1988

[30] Foreign Application Priority Data

Mar. 24, 1987 [JP] Japan .................................. 62-69982

[51] Int. Cl.$^4$ ............................................. C07C 45/28
[52] U.S. Cl. .................................... 568/321; 568/311; 585/468

[58] Field of Search ........................ 585/468; 568/321

[56] References Cited

U.S. PATENT DOCUMENTS

| | | | |
|---|---|---|---|
| 3,038,940 | 6/1962 | Serres et al. ......................... | 568/321 |
| 3,642,906 | 2/1972 | Kahn ..................................... | 568/321 |
| 4,731,483 | 3/1988 | Shimizu et al. ..................... | 568/321 |
| 4,734,528 | 3/1988 | Shimizu et al. ..................... | 568/321 |

OTHER PUBLICATIONS

Olah et al, J.A.C.S., vol. 84, pp. 1688–1695 (1962).

*Primary Examiner*—James H. Reamer
*Attorney, Agent, or Firm*—Scully, Scott, Murphy & Presser

[57] ABSTRACT

3-Ethylbenzophenone is prepared by oxidizing a by-product heavy oil fraction produced in the production of ethylbenzene using ZSM-5 type synthetic zeolite catalyst, without splitting carbon-to-carbon bonds. 3-Ethylbenzophenone is a starting material for synthesis of medicines, etc.

7 Claims, No Drawings

PROCESS FOR PREPARING 3-ETHYLBENZOPHENONE

DESCRIPTION

1. Technical Field

This invention relates to a process for preparing 3-ethylbenzophenone. More particularly, this invention relates to a method to produce 3-ethylbenzophenone represented by the following formula (I) which comprises oxidizing a heavy oil fraction produced as a by-product in the preparation of ethylbenzene using ZSM-5 type synthetic zeolite catalyst, without splitting carbon-to-carbon bonds, said 3-ethylbenzophenone is a key starting material for synthesis of medicines and perfumes.

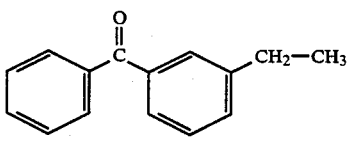

2. Background Art

The following method, for example, is known as the process for preparing 3-ethylbenzophenone.

That is, 3-ethylbenzophenone is obtained by Friedel-Crafts alkylation using benzophenone and diethyl sulfate in the presence of aluminum chloride (Spanish Patent No. 452500). According to this Spanish Patent, ketoprofen (trade name) as a medicine such as anti-inflammatory agent is synthesized. In this method, in spite of the use of highly pure starting materials, the refining is difficult because many kinds of by-products are formed, in addition, its yield is low.

Furthermore, it is proposed to produce 3-ethylbenzophenone by oxidizing the heavy by-product oil which is obtained from the alkylation of benzene with ethylene using aluminum chloride as an alkylation catalyst. However, it is necessary to carry out intensive oxidation with aqueous nitric acid, which is accompanied by the splitting of carbon-to-carbon bonds because the alkylation catalyst is aluminum chloride and therefore the composition of the by-product oil is different from that of the present invention. On account of the intensive oxidation, the yield of the aimed product is low and also it involves a danger of the generation of much explosive nitro compound.

Accordingly, the object of the present invention is to provide a method for synthesizing highly pure 3-ethylbenzophenone inexpensively.

DISCLOSURE OF INVENTION

The present invention relates to a process for inexpensively preparing highly pure 3-ethylbenzophenone.

In short, the process for producing highly pure 3-ethylbenzophenone comprises the step of oxidizing a starting material of a fraction containing (3-ethylphenyl)phenylmethane which is by-produced in the process to prepare ethylbenzene by reacting benzene with ethylene, without splitting carbon-to-carbon bonds.

In the following, the preparation method will be described in more detail.

(Alkylation)

In the preparation of ethylbenzene, benzene is alkylated with ethylene in the presence of an alkylation catalyst to obtain an alkylation product mainly containing unreacted benzene, ethylbenzene, polyethylbenzene and heavier products. This alkylation can be carried out by well known liquid phase alkylation method or gas phase alkylation method. The molar ratio of benzene to ethylene to be used may be about 25:1 to 1:5, preferably about 10:1 to 1:1.

The reaction is generally carried out in gas phase. For example, in the gas phase reaction, starting materials for alkylation are reacted by passing them through ZSM-5 type catalyst at a temperature in the range of about 250° to 650° C., preferably about 300° to 550° C. and under a pressure in the range of atmospheric pressure to 100 kg/cm$^2$, preferably atmospheric pressure to 70 kg/cm$^2$ and at a space velocity of WHSV in the range of 1 to 500, preferably 1 to 300.

As the result of such alkylation, alkylation products of unreacted benzene, ethylbenzene, polyethylbenzene and heavier products are obtained. If desired, the catalyst is previously removed.

The by-product oil is obtained by removing unreacted benzene, ethylbenzene and at least a part of polyethylbenzene form the alkylation products obtained as the above.

The synthetic zeolite catalyst used in the present invention is crystalline synthetic aluminosilicate zeolite of 20 or higher in molar ratio of $SiO_2/Al_2O_3$ and the inlets of main pores thereof are composed of ten-membered oxygen rings. Such a zeolite is exemplified by ZSM-5 type synthetic zeolites having the inlets of main pores composed of ten-membered oxygen rings as well as zeolite zeta 1 and zeolite zeta 2. That is, the zeolites used in the present invention are characterized in that the inlets of main pores are composed of ten-membered oxygen rings. Conventional synthetic zeolites such as zeolite A and erionite have eight-membered oxygen rings, meanwhile, mordenite, zeolite X and zeolite Y have twelve-membered oxygen rings.

These conventional zeolites having eight-membered oxygen rings or twelve-membered oxygen rings are not suitable for the method of the present invention because the structure of them are different from the one used in the present invention.

Any of crystalline synthetic aluminosilicates as far as they are 20 or higher in molar ratio of $SiO_2/Al_2O_3$ and the inlets of main pores thereof are composed of ten-membered oxygen rings can be used as the crystalline synthetic zeolite in the present invention. Especially preferable ones are ZSM-5 type synthetic zeolites known as ZSM-5, ZSM-11, ZSM-22, ZSM-23, ZSM-35, ZSM-38 and ZSM-48. These ZMM-5 type synthetic zeolites have the structural characteristic that the inlets of main pores are composed of ten-membered oxygen rings. Furthermore, especially preferable synthetic zeolite is ZSM-5. The compositions and methods for preparing these ZSM-5 type zeolites are disclosed in the following patent gazettes.

ZSM-5: U.S. Pat. No. 3,702,886
ZSM-11: U.S. Pat. No. 3,709,979 and Japanese Patent Pub. No. 53-23280
ZSM-22: U.S. Pat. No. 4,481,177
ZSM-23: U.S. Pat. No. 4,076,842 and ditto No. 4,490,342
ZSM-35: Japanese Laid-Open Patent Publication No. 53-144500
ZSM-38: U.S. Pat. No. 4,046,859
ZSM-48: U.S. Pat. No. 4,423,021

Zeolite Zeta 1: Japanese Laid-Open Patent Publication No. 51-67299

Zeolite Zeta 2: Japanese Laid-Open Patent Publication No. 51-67298

The synthetic zeolite having the structural characteristic that the inlets of main pores are composed of ten-membered oxygen rings, has usually a high molar ratio of $SiO_2/Al_2O_3$ and the value is generally 20 or higher. In some case, the molar ratio of $SiO_2/Al_2O_3$ is very high, for example, the synthetic zeolite having the molar ratio as high as 1600 can be effective. Furthermore, it is possible to use in some case the zeolite having a value close to infinity in the molar ratio of $SiO_2/Al_2O_3$ which does not substantially have aluminum. Such "high-silica" zeolites are also included in the definition of the present invention. This molar ratio of $SiO_2/Al_2O_3$ can be determined by an ordinary analytical method such as atomic absorption spectrum analysis. This ratio is represented as close as possible to the ratio in the hard skeleton in zeolite crystal but the aluminum in cation form or other forms contained in binder or channels are excluded.

The structure of ten-membered rings in the inlets of main pores generally confirmed by X-ray diffractiometry. For example, ZSM-5 type synthetic zeolite which is suitable as the catalyst in the present invention exhibit characteristic X-ray diffraction patterns particular to them (cf: the foregoing patent gazettes in detail).

It is, however, possible to use values of constraint indexes in place of the X-ray diffractiometry. That is, the ten-membered oxygen ring in the present invention can be defined as the zeolite having constraint indexes of 1 to 12. By the way, the practical determination method of the constraint index is described in Japanese Laid-Open Patent Publication No. 56-133223. This index shows the degree that the micro pore structure of zeolite crystal restrains the access of molecules having a cross sectional area larger than that of n-paraffin. In the determination, as disclosed in the same reference, n-hexane and 3-methylpentane are adsorbed by zeolite under certain conditions and the index is calculated from the adsorbed values.

Typical values of the constraint indexes are as follows:

|  | Constraint Index |
| --- | --- |
| ZSM-5 | 8.3 |
| ZSM-11 | 8.7 |
| ZSM-35 | 4.5 |
| Amorphous Silica-Alumina | 0.6 |

The method for preparing zeolite in the present invention will be described with reference to the synthesis of ZSM-5. A mixture containing reactants of tetrapropylammonium hydroxide or tetra-n-propylammonium bromide, sodium oxide, aluminum oxide, silicon oxide and water, is prepared in the first place. The composition may be made with the range as disclosed in the foregoing reference. The reaction mixture is then subjected to hydrothermal synthesis by heating. After the synthesis, the obtained crystal is baked in the air to obtain zeolite ZSM-5 catalyst. Aluminum oxide is used herein, however, it is also proposed to synthesize ZSM-5 containing substantially no aluminum atom. In the above method, tetrapropylammonium hydroxide or tetra-n-propylammonium bromide is used, however, it is also proposed as the method for synthesizing ZSM-5 to use several other organic cations or organic compounds as their precursors in place of them. Such compounds are exemplified by ammonia, trialkylmethylammonium cation, triethyl-n-propylammonium cation, $C_2$ to $C_9$ primary monoalkylamine, neopentylamine, di- and trialkylamine, alkanolamine, $C_5$ to $C_6$ alkyldiamine, $C_3$ to $C12$ alkylenediamine, ethylenediamine, hexamethylenediamine, $C_3$ to $C_6$ diol, ethylene or propylene glycol, 1,4-dimethoxycyclohexane, hydroquinone, ethylene oxide and ammonia, n-dodecylbenzene sulfonate, cyclopentadienyl phthalocyanine complex, 2-aminopyridine, ethylene glycol dimethyl ether, dioxane, dioxolan, tetrahydrofuran, and carboxylic acids such as tartaric acid.

Furthermore, it is also proposed that, without adding organic cations or organic compounds as the precursor thereof as described above, ZSM-5 is added as the seeds in crystallization.

The zeolite used for the reaction contains metallic ions such as sodium ions which come from the reaction materials in synthesis. Besides the alkali metals such as sodium, it is possible to use the ones which are ion exchanged by other metals of alkaline earth metals such as calcium and magnesium and other trivalent metallic ions. Furthermore, crystalline synthetic aluminosilicate zeolite such as ZSM-5 type zeolite which is modified by impregnating it with magnesium, boron, potassium, phosphorus or their compounds, can also be used. These ion exchange and modification can be carried out according to conventional methods.

As described above, the crystalline synthetic zeolite of the present invention can contain various kinds of metals. However, the synthetic zeolite which is desirable for the method of the present invention is the so-called hydrogen-type zeolite (HZSM-5) or acid-type zeolite in which the metallic ions are exchanged by hydrogen ions. Typical hydrogen-type zeolite is prepared by a process such that the catalyst containing the organic cations used in the catalyst preparation is heated for instance at about 540° C. for 1 hour in an inert atmosphere and it is then subjected to ion exchange with an ammonium salt or a mineral acid such as hydrochloric acid, and it is baked, for example, at about 540° C. to activate, thereby obtaining the what is called hydrogen-type zeolite.

If desired, the zeolite may be further subjected to steam treatment or coking treatment.

Through the above described process, benzene is alkylated with ethylene to obtain a reaction mixture of unreacted benzene, ethylbenzene, polyethylbenzene and heavier components. This heavier components contains (3-ethylphenyl)phenylmethane as well as other tarry substances.

A fraction containing (3-ethylphenyl)phenylmethane is recovered by distillation, preferably by reduced pressure distillation from the above reaction product directly, or by recovering the heavier components once and then distilling it again. Anyhow, the fraction containing (3-ethylphenyl)phenylmethane is recovered as a fraction mainly containing the components in the range of 288° to 295° C. in boiling point (atmospheric pressure basis).

Incidentally, the above alkylation reaction is exemplified by the ethylbenzene preparation using the zeolite catalyst made by Mobil Oil Corp., which is widely put into practice in industry, and the ethylbenzene is used for preparing styrene by dehydrogenation.

(Oxidation Reaction)

In the present invention, the fraction containing (3-ethylphenyl)phenylmethane is oxidized with an oxidizing agent to obtain 3-ethylbenzophenone.

In this oxidation, it is inevitable that the oxidation is carried out without splitting the carbon-to-carbon bonds. In the oxidation which is accompanied by the splitting of carbon-to-carbon bonds, the formation of carbon oxide such as carbon dioxide is observed.

In the above oxidation, known oxidation methods can be used in which methylene group, especially that of diphenylmethane structure is oxidized to ketone. For example, it is exemplified by the oxidation with molecular oxygen in the presence of an oxidation catalyst and the oxidation using an oxidizing agent such as permanganate, manganese dioxide, chromate, bichromate, lead tetraacetate, periodate, ruthenium tetraoxide, osmium tetraoxide, hydrogen peroxide, selenium dioxide, chlorite or hypochlorite, ozone and the mixtures of them.

The catalyst used in the oxidation with molecular oxygen are exemplified by the salts of metals and mixtures of them, which metals are selected from the groups VI-B, VII-B and VIII of the periodic table such as chromium, manganese, tungsten, molybdenum, platinum, palladium, cobalt, nickel, iron, rhodium and ruthenium. Among them, the salts of cobalt, iron, manganese and chromium are preferable. As the salts, for example, the salt or complex of saturated carboxylic acid such as naphthenic acid, and diketone such as acetylacetone are preferable. The suitable quantity of a catalyst to be used is 0.05 to 10% by weight relative to the quantity of reactants. As the molecular oxygen, pure oxygen or the air can be used, or it is possible to supply the reaction system with a mixture of pure oxygen and other inert gases.

The reaction temperature in the oxidation using molecular oxygen is 30° to 250° C., and preferably 50° to 200° C. In the case that the reaction temperature is lower than 30° C., the rate of reaction is very low, while in the case that the reaction temperature is above 250° C., the selectivity to the aimed product is seriously lowered, both of which are not desirable.

In order to improve the efficiency in the contact with an oxidizing agent, a solvent can be used. Such a solvent is exemplified by water, acetone, alcohols such as tert-butyl alcohol, glacial acetic acid, acetic acid, isooctane, benzene, chloroform and pyridine and the mixture of them.

The use quantity of oxidizing agent such as permanganate is at least 1 equivalent, preferably more than 1.5 equivalent, to the raw material. There is not especially the upper limit of the use quantity, however, the quantity of more than 10 equivalent is not desirable because it is only uneconomical. The temperature of oxidation using the oxidizing agent is 0° to 200° C. and preferably 30° to 150° C. The reaction cannot proceed at temperatures below 0° C., while by-products are formed and the selectivity to the aimed product is seriously lowered at temperatures above 200° C., both of which are not desirable.

By this reaction, the methylene group of diphenylmethane structure in (3-ethylphenyl)phenylmethane is oxidized to carbonyl group and 3-ethylbenzophenone is produced in one step reaction, which can be easily refined by distillation.

As described above, because the raw material fraction of the present invention is the one which is by-produced in the ethylbenzene preparation, (3-ethylphenyl)phenylmethane can be obtained very inexpensively.

Furthermore, because the material relating to a specific process is used as a starting material, the o-isomer of (ethylphenyl)phenylmethane is not contained. Moreover, because the p-isomer can be easily separated by distillation, highly pure (3-ethylphenyl)phenylmethane containing no position isomer (nuclear substitution) can be obtained. Still further, because the raw material fraction in the present invention is recovered as a fraction in the range of 288° C. to 295° C. in boiling point (atmospheric pressure basis), it inevitably contains impurities such as polyalkylbenzene which is difficultly separated from (3-ethylphenyl)phenylmethane, however, in the oxidation of the mixture, they hardly react or, even when they are reacted, they are converted into compounds which can be easily separated. Meanwhile, (3-ethylphenyl)phenylmethane in the raw material is converted into ketone of 3-ethylbenzophenone by oxidation which can be easily separated. Therefore, highly pure 3-ethylbenzophenone can be obtained from the specific fraction containing impurities.

Furthermore, because the the methylene group between 2 phenyl groups of (3-ethylphenyl)phenylmethane is easily and specifically oxidized, the oxidation can be carried out in a high yield without difficulty.

BEST MODE FOR CARRYING OUT THE INVENTION

In the following, the present invention will be described in more detail with reference to examples, however, the present invention is not limited only to these examples.

(EXAMPLE)

(Alkylation)

(1) Preparation of Raw Material Fraction

To a stainless steel-made continuous flow reaction vessel was added 100 g of a synthetic zeolite ZSM-5 (H-type, $SiO_2/Al_2O_3$ molar ratio=60) and alkylation of benzene with ethylene was carried out under the following conditions.

| Reaction Temperature: | 450° C. |
| Pressure: | Atmospheric pressure |
| Ethylene/Benzene: | 0.2 (molar ratio) |
| WHSV: | 4.5 $hr^{-1}$ |

The obtained reaction mixture was distilled and heavier components were recovered in a yield of 2.5% by distilling off the unreacted benzene, ethylbenzene and polyethylbenzene.

Then, a fraction of 288° to 293° C. in boiling range (atmospheric pressure basis) was obtained from the recovered heavier components by reduced pressure distillation.

This fraction contained (3-ethylphenyl)phenylmethane. According to analysis, the content of (3-ethylphenyl)phenylmethane was 87% by weight.

(Oxidation)

(2) Preparation of 3-Ethylbenzophenone (1)

In 200 ml of water, 19.7 g of the fraction containing (3-ethylphenyl)phenylmethane obtained in the above alkylation was suspended. With stirring the suspension, 2 liter of an 1.6% aqueous solution of potassium permanganate was dropped. After the dropping, the stirring was continued for about 10 hours at room temperature. After this mixture was acidified with concentrated sulfuric acid, sodium hydrogensulfite powder was added until the reaction mixture became transparent from brown and it was extracted with benzene. After drying the benzene layer with anhydrous magnesium sulfate, 3-ethylbenzophenone was obtained in a yield of 97% by reduced pressure distillation.

(3) Preparation of 3-Ethylbenzophenone (2)

To a 300 ml autoclave with a stirrer were fed 100 g of the fraction containing (3-ethylphenyl)phenylmethane obtained in the above alkylation and 0.2 g of cobalt naphthenate. Reaction was carried out at 150° C. in reaction temperature and under the pure oxygen pressure of 10 kg/cm$^2$ for 3 days.

After the reaction, it was washed with water and was subjected to reduced pressure distillation to obtain 3-ethylbenzophenone in a yield of 45%.

Incidentally, in the oxidation of the above Preparations (1) and (2), the generation of carbon dioxide was not substantially observed and the reaction was not accompanied by the splitting of carbon-to-carbon bond.

(4) Preparation of 3-Ethylbenzophenone (3)

Oxidation with molecular oxygen was carried out in the like manner as in Preparation of 3-Ethylbenzophenone (2) by replacing the cobalt naphthenate with the catalysts shown in the following table. The results of the reaction are shown also in the following table.

| Experiment No. | Metallic Catalyst | Yield of 3-Ethylbenzophenone (%) |
|---|---|---|
| 1 | Cobalt acetylacetonate | 48 |
| 2 | Manganese naphthenate | 30 |
| 3 | Cobalt 2-ethylhexanoate | 39 |
| 4 | Iron naphthenate | 25 |
| 5 | Chromium naphthenate | 24 |

INDUSTRIAL APPLICABILITY

The present invention relates to the preparation of 3-ethylbenzophenone and, for example, according to the disclosure in Spanish Patent No. 452500, it is possible to prepare ketoprofen (trade name) from the obtained 3-ethylbenzophenone. Furthermore, when 3-vinylbenzophenone is prepared by dehydrogenating 3-ethylbenzophenone, it is converted into the same ketoprofen according to the method disclosed in U.S. Pat. No. 4,329,507. Ketoprofen is a useful medicine as a anti-inflammatory agent or pain-killing agent.

We claim:

1. A process for preparing highly pure 3-ethylbenzophenone, which comprises the steps of: obtaining an alkylation product mainly comprising unreacted benzene, ethylbenzene, polyethylbenzene and heavier components containing (3-ethylphenyl)phenylmethane by alkylating benzene with ethylene in the presence of ZSM-5 type synthetic zeolite catalyst, then recovering by distillation a fraction which contains (3-ethylphenyl)phenylmethane and which mainly comprises the components in the range of 288° to 295° C. in boiling point (atmospheric pressure basis) from said alkylation product, further oxidizing said fraction without splitting carbon-to-carbon bonds, and then recovering 3-ethylbenzophenone represented by the following formula (I) by distillation.

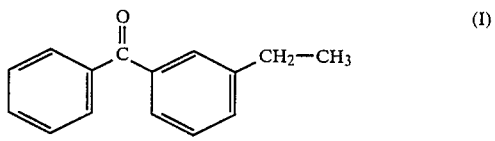

2. The method in claim 1, wherein said oxidation is carried out with molecular oxygen at a temperature of 30° to 250° C. in the presence of a metallic oxidation catalyst containing the metals selected from the groups of VI-B, VII-B and VIII in the periodic table.

3. The method in claim 2, wherein said metal is one member selected from the group consisting of cobalt, iron, manganese and chromium.

4. The method in claim 1, wherein said oxidation is carried out at 0° to 200° C. in the presence of an oxidizing agent selected from permanganate, manganese dioxide, chromate, bichromate, periodate, ruthenium tetraoxide, chlorite or hypochlorite, ozone and mixtures thereof.

5. The method in claim 3, wherein at least one equivalent of said oxidizing agent is used to one mole of (3-ethylphenyl)phenylmethane in the raw material.

6. The method of claim 2 including the following step conducted prior to the recovery of the 3-ethylbenzophenone by distillation:
washing the oxidized fraction with water.

7. The method of claim 4 including the following steps conducted prior to the recovery of the 3-ethylbenzophenone by distillation:
neutralizing the oxidized fraction and extracting the neutralized fraction with an organic solvent.

* * * * *